United States Patent [19]

Rakitin et al.

[11] 4,084,757

[45] Apr. 18, 1978

[54] APPARATUS FOR CONTINUOUS DISINTEGRATION OF CELLS OF MICROORGANISMS

[76] Inventors: Vladimir Jurievich Rakitin, Verkhny Mikhailovsky pereulok, 7, korpus 2, kv. 113; Igor Konstantinovich Fedorov, Bolotnikovskaya ulitsa, 40, korpus 3, kv. 75; Alfred Nikitovich Grigorian, Snaiperskaya ulitsa, 7, kv. 91, all of Moscow; Vitaly Viktorovich Lalov, Sovetskaya ulitsa, 22/49, kv. 12, Moskovskaya oblast, Podolsk; Nina Vasilievna Prokofieva, Botanicheskaya ulitsa, 19, kv. 68, Moscow, all of U.S.S.R.

[21] Appl. No.: 711,951

[22] Filed: Aug. 5, 1976

[51] Int. Cl.² .............................................. B02C 19/00
[52] U.S. Cl. ........................................ 241/301; 241/1
[58] Field of Search .................... 241/1, 2, 5, 39, 301

[56] References Cited

U.S. PATENT DOCUMENTS

| 2,928,614 | 3/1960 | Emanuel et al. | 241/1 |
| 3,165,266 | 1/1965 | Blum et al. | 241/1 |
| 3,309,032 | 3/1967 | Filz et al. | 241/1 |
| 3,458,139 | 7/1969 | Edebo | 241/39 |
| 3,556,414 | 1/1971 | Eberly, Jr. | 241/1 |
| 3,887,144 | 6/1975 | Schaeffer | 241/1 |

*Primary Examiner*—Granville Y. Custer, Jr.
*Attorney, Agent, or Firm*—Steinberg & Blake

[57] ABSTRACT

To effect disintegration of cells of microorganisms such as yeast, bacteria, and fungi, a suspension of cells is presaturated with a compressed gas and then passed through one or more disintegration units containing a plate valve seat and valve member urged toward each other. The disintegration unit can be attached to a mechanical vibrator-shaker. At the inlet of said disintegration unit there are two thick-wall vessels, i.e. a mixing vessel to effect intermixing of the suspension and compressed gas and a homogenizing vessel to maintain the suspension under pressure. When the suspension is passed through a throttling slit formed between the valve seat and valve member, cell shells are intensively broken due to the internal pressure.

8 Claims, 2 Drawing Figures

APPARATUS FOR CONTINUOUS DISINTEGRATION OF CELLS OF MICROORGANISMS

The present invention relates to a process for continuous disintegration of microorganism cells which is required, e.g. in fermentation, food and pharmaceutical industries; the present invention also relates to an apparatus for continuous disintegration of a suspension of microorganism cells such as yeast, bacteria, fungi. The apparatus can be employed, as a multi-purpose apparatus, in microbiological industry for the preparation of disintegrates of cells having an increased digestibility and for replacement of the plasmolysis stage as well as for isolation of intracellular biopolymers such as proteins, enzymes, nucleic acids and the like.

Known in the art are numerous processes and apparatus for disintegration of microorganism cells which find an extensive use in laboratorial practice.

However, a large-scale implementation of disintegrators for these purposes is restricted to two processes and corresponding apparatus. The former comprises a hydroextrusion process involving compression of a suspension of cells under pressures of up to 3,000 atm, followed by pressure release down to the atmospheric value which is effected in one or more stages. A corresponding apparatus has been developed by an American corporation "Manton Gaulin". It is available with the output of up to 10 m$^3$/hr.

This apparatus is mainly intended for homogenization of milk, milk products, juices, etc., and during its practical application for disintegration of cells of microorganisms has revealed that its performances depend on pressure values and rate of variation thereof.

This apparatus contemplates the use of high pressures (up to 3,000 atm), large energy and metal consumption; furthermore, the process of cell disintegration involving one-stage pressure drop is less economically efficient.

Another large-scale process for disintegration of microorganism cells contemplates the use of a ball mill, i.e. grinding of cells with milling bodies (carborundum, glass and the like) with a diameter of from 0.5 to 0.75 mm in a cylindrical cooled chamber provided with beaters rotating at a high speed.

Such disintegrators of the "Dyno-Mill" type are available from "WAB", a Swiss company; they have capacity of up to 0.3 m$^3$/hr with respect to a suspension of cells. This apparatus also features high energy consumption, substantial overheating, grinding of milling bodies themselves, rather short reliable service life, difficulty of its commercial implementation.

Also a proposed apparatus is based on the "decompression" principle and comprises two series-connected thick-wall vessels, i.e. mixer and homogenizer.

The mixing vessel has inlet pipes for a suspension of cells fed from a metering pump and for compressed air; it is also provided with a level control device of, for example, float type. A cell suspension saturated under a gas pressure of 100 to 120 atm is passed through the homogenizer and released to atmospheric pressure in the disintegrating means consisting of two casings, an upper one provided with a plate seat and sealing gasket and a lower one provided with a seat having a circular boss resting on a shock-absorber. The casings are secured to each other by means of three studs with centering washers and adjusting screws.

This prior art apparatus has some disadvantages residing in difficulties encountered in the control of said disintegration means, necessity of applying great forces and a limited capacity with respect to cell suspension (about 100 l/hr).

Also known in the art is an apparatus (cf. U.S. Pat. No. 2,190,689; 1940) intended for disintegration of yeast cells. It consists of the following principal units: a reservoir for "activation" of yeast, a pump for feeding the suspension, via a cooler (heat-exchanger) into a colloidal mill, a high-pressure compressor, heater (heat-exchanger) and a spraying head and a collector which can operate under atmospheric pressure or under vacuum.

There is USSR Pat. No. 477742, Cl. BO2C, 19/00 C12k, 1/00 Inventor's Certificate disclosing an apparatus for disintegration of biological materials developed in "VNIISintezbelok" by a group of authors. This apparatus comprises a thick-wall cylindrical shell, whereinto a working material is placed and gas pressure is created with subsequent release of this pressure through a hollow valve with a large cross section into a receiving vessel. The valve lifting and pressure release is effected by means of an arm mounted over the receiving vessel.

While the former apparatus features such disadvantages as multi-stage process, complicated process equipment and difficulties in the process control, the latter features periodic character of the process of disintegration of biological materials.

The use of cooling and heating units and a low-efficient colloidal mill in the former case and periodic operation conditions in the second one cannot be regarded effective from both economic and technological considerations.

It is an object of the present invention to provide a process and an apparatus for a continuous disintegration of cells of microorganisms which would make it possible to substantially intensify the disintegration process by ensuring a continuous technological cycle.

It is another object of the present invention to provide a process and an apparatus for a continuous disintegration of cells of microorganisms which would make it possible to ensure an automatically controlled disintegration process and discontinuous operation for a prolonged time period.

Still another object of the present invention is to provide a process and an apparatus for a continuous disintegration of cells of microorganisms which would make it possible to substantially stabilize the disintegration process, while ensuring a continuous technological cycle.

A further object of the present invention is to provide a process and an apparatus for a continuous disintegration of cells of microorganisms which would make it possible to break cell shells of different kinds of microorganisms in a continuous technological cycle.

Another object of the present invention is to provide a process and an apparatus for a continuous disintegration of cells of microorganisms which would make it possible to simulate theoretically the continuous disintegration process to put into commercial practice.

Still another object of the present invention is to provide a process and an apparatus for a continuous disintegration of cells of microorganisms which would make it possible to substantially improve technical and economic parameters of the continuous disintegration process.

Still another object of the present invention is to provide a process and an apparatus for a continuous disintegration of cells of microorganisms which would make it possible to obtain products of microbiological synthesis for feeding purposes having an increased digestibility on a commercial scale under continuous operation conditions.

Still another object of the present invention is to provide a process and an apparatus for a continuous disintegration of cells of microorganisms which would make it possible to recover intracellular biopolymers under continuous operation conditions.

Still another object of the present invention is to provide a process and an apparatus for a continuous disintegration of cells of microorganisms which would make it possible to substantially simplify the process equipment thus reducing metal consumption for the continuous integration apparatus.

A further object of the present invention is to provide a process and an apparatus for a continuous disintegration of cells of microorganisms which would make it possible to substantially increase the reliable service life under continuous operation conditions for prolonged time periods.

One more object of the present invention is to provide a process and an apparatus for a continuous disintegration of cells of microorganisms which would make it possible to increase efficiency of breaking of cell shells per one cycle under continuous operation conditions.

Still another object of the present invention is to provide a process and an apparatus for a continuous disintegration of cells of microorganisms which would make it possible to substantially reduce the operation pressure of disintegration, while ensuring continuous process conditions.

These and other objects of the present invention are accomplished by an improved apparatus for a continuous disintegration of cells of microorganisms such as yeast, bacteria and fungi by way of throttling an aqueous suspension of cells of microorganisms ensuring mechanical breaking of the cell shells. This apparatus has a specific feature residing in that an aqueous suspension of cells of microorganisms is presaturated with a compressed gas under a controlled pressure so that at least one volume of the gas be dissolved in one volume of the suspension; whereafter the gas-saturated suspension is maintained under the saturation pressure for a period sufficient to ensure a uniform distribution of the gas over the entire suspension volume; the thus-prepared suspension is continuously passed through a disintegration unit, wherein upon passing the suspension through a narrow throttling slit an abrupt pressure drop is developed in the cells and shells thereof become broken by the internal pressure.

This technical approach makes it possible to substantially intensify the process of cell disintegration owing to the above-mentioned pre-saturation of the suspension of cells with a gas under pressure in a mixing vessel.

One embodiment of the present invention comprises an apparatus which is characterized in that it consists of two series-connected pressurized thick-wall vessels; one of these is a mixing vessel for mixing a suspension of cells with a compressed gas, while another vessel is intended for maturation of the gas-saturated suspension. The apparatus also has a disintegration means consisting of at least one unit comprising two valve members facing each other and a mechanism for bringing them together with the formation of a controlled throttling slit, one of said valve members being constantly spring-loaded.

This technical solution makes it possible to substantially intensify the process of cell disintegration owing to that the mixing vessel is provided with a level control device which creates a gas cushion over the suspension mass being saturated.

Another feature of the apparatus according to the present invention is characterized in that the disintegration unit involves two flange-like casings, the former being provided with a plate valve seat, while the latter has a valve member with at least one annular sharp-edged projection resting at its edge against the valve seat, said latter flange-like casing also having a resilient shock absorber and both casings being secured to each other by means of a tightening thread mechanism.

This technical solution makes it possible to substantially intensify the process of cell disintegration owing to the fact that the mixing vessel is series-connected with the vessel for maturation of the gas-saturated suspension.

According to a further feature of the present invention, the apparatus for a continuous disintegration of microorganism cells contains several disintegration units of the same structural arrangement.

This technical solution makes it possible to substantially intensify the process of cell disintegration owing to the fact that the disintegration unit contains two valve members facing each other with an adjustable throttling slit therebetween, one of the members being constantly spring-loaded, and said unit is provided with a mechanism for bringing the valve members together.

Still another feature of the present invention is characterized in that the flange-like casing provided with a shock-absorber has several concentric annular projections of said valve member and a hole in its central portion for the discharge of disintegrated cells, while the other flange-like casing has a valve seat provided with a plurality of radial channels for supplying the suspension of cells into the zone formed between said annular projections.

Such technical solution makes it possible to substantially intensify the process of cell disintegration due to the fact that the disintegration unit contains two flange-like casings, the former having a valve seat with a plurality of radial channels for the suspension supply, while the latter having a valve member with several concentric annular sharp-edged projections and a hole in its central portion; said second valve member rests against the first valve seat; both casings being secured to each other by means of an adjustable tightening thread mechanism; one of said casings having a hole in its central portion.

According to still another embodiment of the present invention, the disintegration unit of the apparatus has a mechanical vibrator-shaker attached to one of said flange-like casings.

This technical solution makes it possible to substantially intensify the process of cell disintegration owing to the fact that the disintegration unit is provided with a mechanical vibrator-shaker attached to one of the flange-like casings.

According to a further feature of the present invention, the apparatus is characterized in that at the outlet of said disintegration unit said suspension-mixing vessel has a level control device maintaining a predetermined level of a gas cushion over the suspension mass being saturated.

This technical solution makes it possible to substantially intensify the process of cell disintegration owing to the fact that the continuous disintegration apparatus involves several disintegration units of the same structural arrangement.

The present invention is further illustrated by the following detailed description of an embodiment thereof with reference to the accompanying drawings, wherein.

The apparatus according to the present invention for a continuous disintegration of cells of microorganisms such as yeast, bacteria and fungi by way of throttling an aqueous suspension of microorganism cells ensuring mechanical breaking of cell shells comprises pre-saturation of said aqueous suspension of microorganism cells with a compressed gas under a controlled pressure so that at least one volume of the gas is dissolved in one volume of the suspension. Thereafter, said gas-saturated suspension is maintained under the saturation pressure for a period sufficient to obtain a uniform saturation of the suspension with said gas over the entire suspension volume. The thus-prepared suspension is continuously passed through a disintegration unit, wherein upon passing the suspension through a narrow throttling slit a sharp pressure drop in cells is created thus breaking the cell shells due to the internal pressure.

Figure 1:
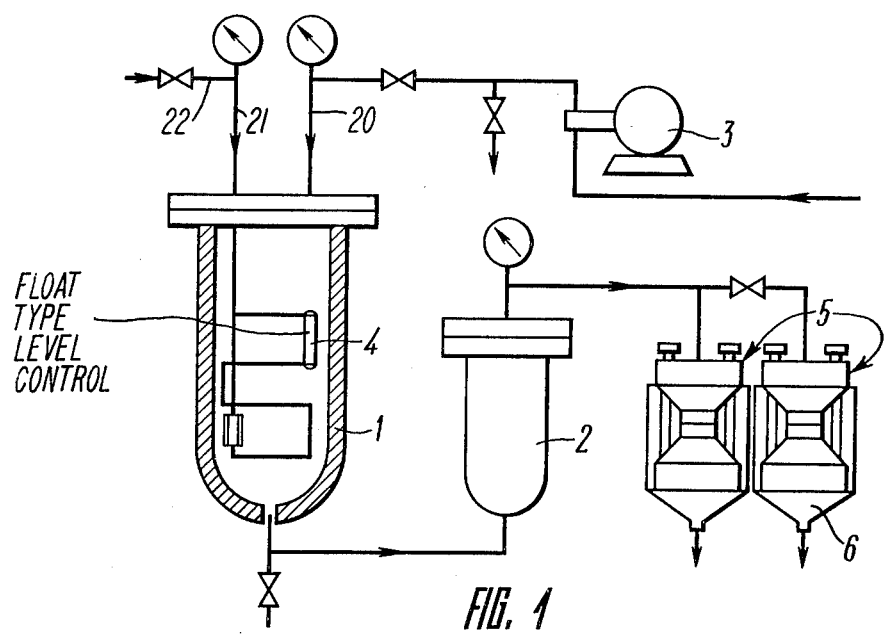
FIG. 1 is a schematic illustration of the apparatus for a continuous disintegration of cells of microorganisms according to the present invention.

The apparatus for a continuous disintegration of a suspension of microorganism cells according to the above-described process (FIG. 1) consists of two cylindrical thick-wall vessels including a mixing vessel 1 and a homogenizing vessel 2. The upper section of the mixing vessel has inlet pipes 20 and 21 respectively for the supply of said suspension of cells by means of a metering pump 3 and for the supply of a compressed gas via a high-pressure line 22. The mixing vessel 1 has mounted therein a level control device 4, of, for example, a float type.

The lower section of the mixing vessel 1 has an outlet communicating with the lower section of homogenizing vessel 2. The upper portion of vessel 2 has an outlet communicating with a plurality of disintegration units 5 each mounted inside a collecting reservoir 6.

In its general arrangement, each disintegration unit 5 consists of two flange-like casings one of which is provided with a plate valve seat having an annular peripheral gasket, while the other casing has a valve member with at least one annular sharp-edged projection pressing against the valve seat. The second flange-like casing contains a resilient shock-absorber and both casings are secured to each other by means of an adjustable tightening thread mechanism.

Figure 2:
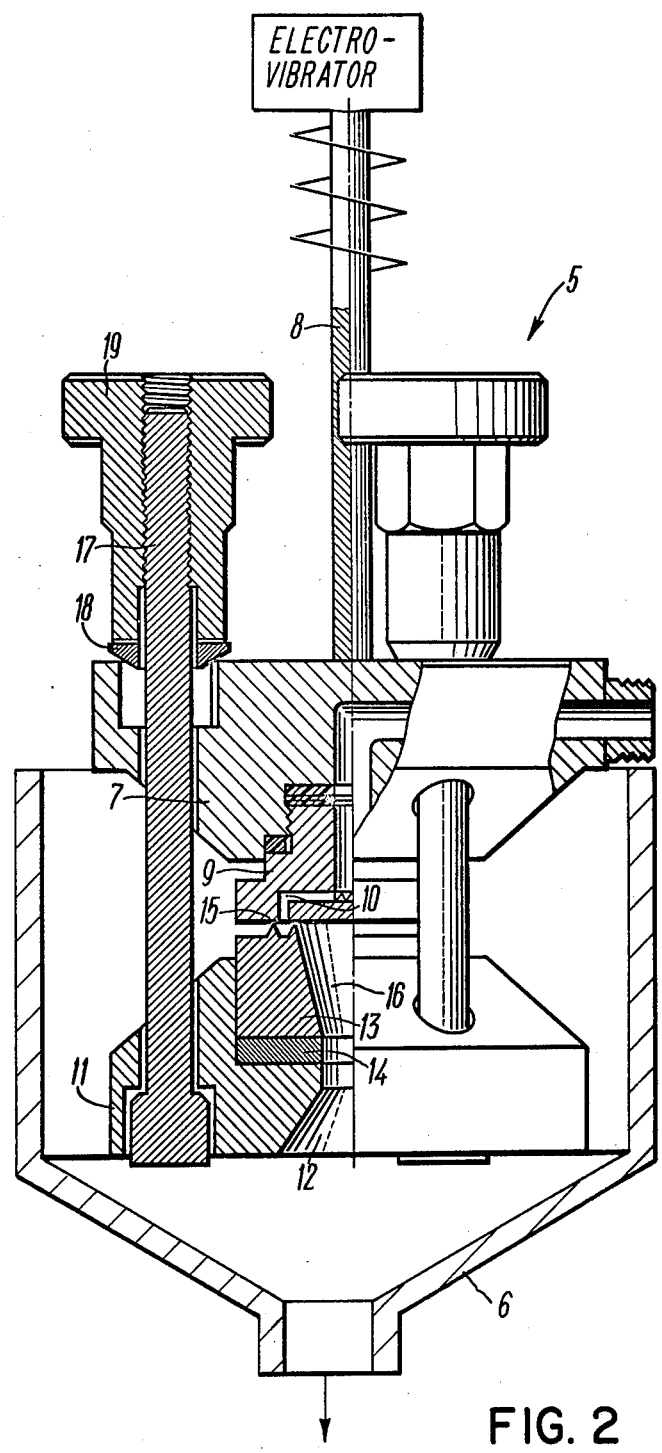
FIG. 2 is a schematic partly sectional illustration of a disintegration unit of the apparatus shown in FIG. 1.

In particular, each disintegration unit 5 (FIG. 2) consists of two flange-like casings: the upper one 7 provided in its upper section with a shaker 8 of, for example, electrovibrator type; its lower portion is provided with a plate valve seat 9 formed with a plurality of radial channels 10; the lower casing 11 has a hole 12 in its central section which is provided with a shock-absorber 14 serving to constantly spring-load a valve member 13 resting upon the shock-absorber 14 and having a pair of concentric annular sharp-edged projections 15 as well as a hole 16 in its central section. Both casings are secured to each other by an adjusting means including three studs 17 with centering washers 18 and adjusting nuts 19 which comprise a mechanism for bringing the seat 9 and valve member 13 together with a force determined by the extent to which shock-absorber 14 is compressed by the adjusting means 17-19.

By means of this mechanism for bringing the valve components 9 and 13 together it is possible to control the width of the throttling slit formed between said components 9 and 13. Thus, a gas-saturated cell suspension is fed at a given pressure through the channels 10 into the chamber defined between the sharp-edged annular projections 15. The extent to which the shock-absorber 14 is compressed is adjusted by way of the adjusting means 17-19 so that the pressure of the gas-saturated cell suspension will be sufficient to compress the shock-absorber 14 beyond the extent to which it is compressed by the adjusting means 17-19, thus causing the gas-saturated cell suspension to displace valve member 13 slightly away from valve seat 9 so as to define in this way during operation of the apparatus between the bottom surface of valve seat 9 and the edges of projections 15 narrow slits through which the suspension escapes to have its pressure suddenly reduced to atmospheric pressure while the suspension travelling beyond the projections 15 is collected in the reservoir 6 and discharged therefrom.

The present invention provides an opportunity to operate simultaneously with several structurally identical disintegration units 5 as described hereinbefore.

Operation of the apparatus, i.e. continuous disintegration of microorganism cells is effected in the following manner: compressed air is supplied via a high-pressure line 22 from a pressure bottle or compressor and metering pump 3 is switched on to continously supply a suspension of cells sequentially into the mixing vessel 1 and homogenizing vessel 2. As the liquid level in the mixing vessel 1 starts to rise, the float of level control device 4 also rises and opens, thereby, a valve for the compressed air which is bubbled through the suspension under pressure.

The gas-saturated suspension is continuously passed into the disintegration units 5, wherein the pressure is released down to the atmospheric value; thereafter it is collected in collecting reservoirs 6 and discharged to the outside. In each unit 5 the cell suspension is fed into said plate valve seat 9 of the upper casing 7 of the unit, passed through the plurality of radial channels 10 into the chamber defined between the double annular projection 15 of the lower valve member 13 and discharged to the outside and inside of the hole 16 and central section of the casing, and then it is collected in the collecting reservoir 6, wherefrom it is discharged to the outside.

During the operation the disintegration pressure is set by means of the adjusting nuts 19. At the same time the shaker 8 of, for example, electrovibrator type mounted on the upper portion 7 of the disintegration unit 5 operates continuously, thus preventing the disintegration unit 5 from clogging.

The apparatus is further operated continuously and automatically ensuring disintegration of a suspension of microorganism cells within the predetermined ranges of flow rates and pressures for lasting time periods.

The apparatus according to the present invention is comparatively simple, reliable, automated, easily duplicated for commercial implemention and makes it possible to effect disintegration of a suspension of microorganism cells continuously and efficiently.

What is claimed is:

1. In an apparatus for disintegrating microorganism cells in a gas-saturated suspension, a disintegrating unit comprising a valve means having a pair of valve components one of which is a valve seat and the other of which is a valve member having at least one elongated projection terminating in an edge which engages said valve seat when the unit is not operating, springloading means operatively connected with at least one of said components for urging the latter toward each other to maintain said edge of said projection in engagement with said valve seat when the unit is not operating, adjusting means operatively connected with said valve means for adjusting the force with which said spring-loading means urges said components toward each other, said components cooperating with each other for defining between themselves a chamber part of which is defined by said projection and a surface of said valve seat which is adjacent said projection, said valve means being formed with a passage communicating with said chamber for feeding said gas-saturated suspension thereto a predetermined pressure sufficient to displace said valve member away from said valve seat in opposition to said spring-loading means to an extent which will define during operation of the disintegration unit between said projection and valve seat a narrow slit through which the suspension flows from said chamber to be suddenly reduced to atmospheric pressure.

2. The combination of claim 1 and wherein said disintegration unit includes a pair of flange-like casings respectively carrying said valve components, said spring-loading means being in the form of a resilient shock-absorber supported by that one of said casings which carries said valve member, and the projection of the latter terminating in a relatively sharp edge, said adjusting means being operatively connected with said casings for urging them toward each other.

3. The combination of claim 1 and wherein the apparatus includes a first thick-walled pressurized vessel for mixing the cell suspension with the gas and a second thick-walled pressurized vessel for receiving the mixed gas-saturated suspension from the first vessel and for maintaining the gas-saturated suspension under pressure, said second vessel communicating with said passage of said disintegration unit.

4. The combination of claim 3 and wherein a plurality of said units communicate with said second vessel for simultaneously receiving the pressurized gas-saturated cell suspension therefrom.

5. The combination of claim 3 and wherein a pair of lines respectively communicate with said first vessel for respectively supplying thereto a cell suspension and a gas under pressure to be mixed therewith in said first vessel, and said first vessle having in its interior a float-control means for maintaining a gas cushion over the suspension in said first vessel.

6. The combination of claim 1 and wherein said valve member includes a pair of concentric annular projections which engage said valve seat when the disintegrating unit does not operate and which define said chamber between themselves, said passage including radial channels formed in the valve seat component and communicating with the chamber defined between said annular projections, said valve member being formed inwardly of said annular projections with a central hole which receives part of the suspension which escapes from said chamber.

7. The combination of claim 1 and wherein a shaker means is operatively connected with said disintegration unit for shaking the same.

8. The combination of claim 1 and wherein a collecting reservoir surrounds said disintegration unit for receiving therefrom the suspension which is at atmospheric pressure.

* * * * *